United States Patent [19]
Jung

[11] Patent Number: 5,832,176
[45] Date of Patent: Nov. 3, 1998

[54] HEATING TYPE ULTRASONIC HUMIDIFIER

[75] Inventor: Woong Jung, Kyeongki-Do, Rep. of Korea

[73] Assignee: Daewoo Electronics Co., Ltd., Rep. of Korea

[21] Appl. No.: 704,980

[22] Filed: Aug. 29, 1996

[30] Foreign Application Priority Data

Aug. 30, 1995 [KR] Rep. of Korea .................. 1995-27570

[51] Int. Cl.⁶ .......................... A61M 16/00; F02M 15/04
[52] U.S. Cl. ............................................. 392/391; 261/142
[58] Field of Search ..................................... 392/386, 391, 392/400–402, 405–406; 261/1, 4, 138, 139, 141, 142, DIG. 65, DIG. 48, DIG. 15

[56] References Cited

U.S. PATENT DOCUMENTS

| | | | |
|---|---|---|---|
| 1,756,053 | 4/1930 | Colton | 392/402 |
| 4,031,171 | 6/1977 | Asao | 261/1 |
| 4,089,915 | 5/1978 | Jackson | 261/142 |
| 4,238,425 | 12/1980 | Matsuoka et al. | 261/DIG. 48 |
| 4,257,989 | 3/1981 | Nishikawa | 261/DIG. 48 |
| 4,752,422 | 6/1988 | Uchida et al. | 261/DIG. 48 |
| 5,067,169 | 11/1991 | Chiu | 392/406 |
| 5,073,967 | 12/1991 | Marino | 392/406 |
| 5,176,856 | 1/1993 | Takahashi et al. | 261/142 |
| 5,464,572 | 11/1995 | Bonzi | 261/DIG. 48 |

*Primary Examiner*—Teresa J. Walberg
*Assistant Examiner*—Sam Paik
*Attorney, Agent, or Firm*—Cushman Darby & Cushman Intellectual Property Group of Pillsbury Madison & Sutro, LLP

[57] ABSTRACT

Disclosed is a heating type ultrasonic humidifier that destroys germs existing in water, and has enhanced efficiency because of heating the water by a heater. The humidifier has a housing having a removable water supply vessel wherein a valve is mounted on a lower end of the water supply vessel installed at a first portion of the housing, and a duct formed at a first side wall of the housing. The housing has a subsidiary water vessel having a water flow pipe, a heater water vessel which has a heater and a discharging pipe, a pressure control device, a pressure valve device, a main water vessel which has an ultrasonic vibrator, a mist conduit pipe, a nozzle, and a motor-blower. Accordingly, the humidifier destroys the germs existing in the water in the heater water vessel because the water is heated by the heater. Furthermore, the water having the temperature above a predetermined value is supplied into the main water vessel from the heater water vessel because the amount of water flowing into the main water vessel is adjusted by the pressure control device and the pressure valve device, so the efficiency of humidifier is enhanced.

20 Claims, 3 Drawing Sheets

HEATING TYPE ULTRASONIC HUMIDIFIER

BACKGROUND OF THE INVENTION

1. Field of the Invention

The present invention relates to a heating type ultrasonic humidifier, more particularly to a heating type ultrasonic humidifier which can destroy germs existing in water by heating the water with a heater, and to a heating type ultrasonic humidifier which has enhanced efficiency because a pressure controlling device installed in the humidifier therein supplies a main water vessel with the water having a temperature more than a predetermined value.

2. Description of the Prior Art

In general, humidifiers are classified into heating type humidifiers and ultrasonic humidifiers. A heating type humidifier sprays water vapor generated from the water in a water vessel into a room by heating the water in the water vessel by a heater. An ultrasonic humidifier sprays water droplets generated from the water stored in a water vessel into a room by an ultrasonic vibrator installed in the ultrasonic humidifier, which converts the water in the water vessel into the water droplets with high frequency energy.

However, the heating type humidifier consumes much electric power because the water in the water vessel is heated by the heater installed in the heating type humidifier therein. Also, the heating type humidifier has a second disadvantage that the time necessary for heating the water in order to generate the water vapor is long, so sufficient water vapor may not be generated within a desired amount of time. Therefore, an ultrasonic humidifier which settles above-mentioned problems is disclosed in U.S. Pat. No. 4,031,171 (issued to Makoto Asao et al.).

FIG. 1 is a cross-sectional view for showing the above-disclosed ultrasonic humidifier. Referring to FIG. 1, the ultrasonic humidifier has an upper cabinet 1 having a rectangular shape and a lower cabinet 2 which is arranged beneath upper cabinet 1. The bottom portion of upper cabinet 1 is open and lower cabinet 2 has a water vessel 3 which is integrally formed with lower cabinet 2 in the central portion of lower cabinet 2. Upper cabinet 1 and lower cabinet 2 are connected to each other through a chassis board 4.

A power transformer 5, a high frequency generator 6, and a motor-blower 7 are fixed on chassis board 4. Motor-blower 7 supplies a space 8 in water vessel 3 with air from outside. A level drop detector 9 is installed at the upper portion of chassis board 4 so that level drop detector 9 is protruded into the water in water vessel 3. Level drop detector 9 is magnetically operated. Level drop detector 9 detects whether the level of water in water vessel 3 has fallen to below a predetermined value. Level drop detector 9 comprises a float guide 9a which is perpendicularly fixed to chassis board 4 and extended in the downward direction, a magnetically operated switch 9b installed in float guide 9a, and a float 9d having two bar magnets 9c inserted in float 9d therein. Float 9d is combined with float guide 9a, to move upward and downward. When float 9d drops below the predetermined level of water according as the level of water in water vessel 3 has fallen, switch 9b is opened so high frequency generator 6 is stopped. When float 9d is in a position above the predetermined level, switch 9b is closed so high frequency generator 6 is operated.

A mist conduit pipe 10 which is comprised of an ultrasonic wave isolating material such as a plastic material is fixed to chassis board 4. The upper portion of mist conduit pipe 10 projects through upper cabinet 1 above upper cabinet 1, and the lower portion of mist conduit pipe 10 extends to near the bottom of water vessel 3 in lower cabinet 2. A nozzle 11 is installed on the upper end of mist conduit pipe 10, to be rotated in all directions. An ultrasonic vibrator assembly 12 is fixed onto the lower end of mist conduit pipe 10. An ultrasonic vibrator (not shown) is installed in ultrasonic vibrator assembly 12. A plurality of holes 10a are formed in the lower peripheral portion of mist conduit pipe 10. Preferably, holes 10a are formed at the position just above the predetermined level of water in water vessel 3. A coaxial cable 13 for supplying the ultrasonic vibrator with high frequency energy, is connected between high frequency generator 6 and ultrasonic vibrator assembly 12. A water supply tank 14 is removably placed in upper cabinet 1. Water supply tank 14 has an outlet pipe 14a projecting into water vessel 3, and a handle 14b for easily removing water supply tank 14 from upper cabinet 1.

A cap 15 having a valve mechanism is installed on the lower end of outlet pipe 14a. The valve mechanism automatically supplies water vessel 3 with water, to maintain the standard level determined by the lower end of cap 15. Upper cabinet 1 is covered with a top plate 16 except at the portion for mounting and removing water supply tank 14. A power switch 17 for keeping power transformer 5 or high frequency generator 6 operative or inoperative, and a lamp 18 kept lighted while power switch 17 is closed, to keep power transformer 5 or high frequency generator 6 operative, are provided on top plate 16.

Hereinafter, the operation of above-described humidifier will be explained.

When the water in water vessel 3 is positioned at the standard level, if power switch 17 is closed on, power transformer 5, high frequency generator 6, and motor-blower 7 are in an operating state, so a high frequency electric power will be fed to the ultrasonic vibrator through coaxial cable 13 from high frequency generator 6. Therefore, a high frequency energy generated from the ultrasonic vibrator is applied to the water in mist conduit pipe 10, to produce mist or water droplet of a diameter less than 5 microns from the water in mist conduit pipe 10.

As shown by an arrow in FIG. 1, the air current fed into the space 8 of water vessel 3 by motor-blower 7, is flowed into mist conduit pipe 10 through holes 10a, and is sprayed with the mist through nozzle 11 into the room. When the water level in water vessel 3 falls down due to generating the mist, the pressure of water vessel 3 is lowered, thereby the water in water supply tank 14 flows into water vessel 3 through outlet pipe 14a by the atmospheric pressure, so the water level recovers to the predetermined water level. If water supply tank 14 is removed, float 9d falls below the predetermined water level according as the water level in water vessel 3 has fallen. In that case, switch 9b is opened to stop the operation of high frequency generator 6 and motor-blower 7. At the same time, the shortage of water in water vessel 3 is automatically informed to a user by the lightening of a warning lamp.

When water supply tank 14 is installed in upper cabinet 1 after water supply tank 14 is filled with water, the water in water supply tank 14 flows into water vessel 3, so the water level in water vessel 3 recovers to the predetermined water level and switch 9b is closed to operate the humidifier.

However, in the above-described ultrasonic humidifier, the human body may be infected by the germs included in the sprayed mist or water droplets because the mist or the water droplets are generated in a state where the germs existing in the water in the water vessel are not sufficiently destroyed. Furthermore, the efficiency of humidifier is lowered because the time needed to generate water droplets by ultrasonically vibrating the water in water vessel without pre-heating the water, is longer.

SUMMARY OF THE INVENTION

Therefore, it is an object of the present invention to provide a heating type ultrasonic humidifier which can destroy the harmful germs existing in water by supplying the heated water by means of a heater to a main water vessel. Another object of the present invention is to provide a heating type ultrasonic humidifier which has enhanced efficiency by supplying a main water vessel with the water that has a temperature more than a predetermined value by controlling the amount of water flowing into the main water vessel with a pressure control device.

To achieve the above objects of the present invention, the heating type ultrasonic humidifier of the present invention has:

a housing having a removable water supply vessel placed on a first portion in the housing, and a duct formed at a first side wall of the housing;

a subsidiary water vessel for receiving water from the water supply vessel, the subsidiary water vessel being installed beneath the water supply vessel at the first portion in the housing;

a heater water vessel for receiving the water from the subsidiary water vessel, the heater water vessel being installed at a second portion in the housing and being connected to the subsidiary water vessel, the heater water vessel having a heating device for heating the supplied water, the heating means being installed on a lower portion of the heater water vessel;

a pressure control device for sealing up the heater water vessel to keep a pressure of the heater water vessel constant, the pressure control means being installed on an upper portion of the heater water vessel;

a main water vessel for receiving the heated water by the heating device, the main water vessel having an ultrasonic vibrator, the main water vessel being connected to the heater water vessel;

a mist conduit pipe for discharging a mist, the mist conduit pipe being formed above the main water vessel; and a motor-blower for supplying the mist conduit pipe with an air through the duct, the motor-blower being mounted on a lower portion of the housing under the main water vessel.

Preferably, the heater water vessel further has i) a backward flow preventing bar for preventing the water supplied from the subsidiary water vessel from backward flowing, the backward flow preventing bar having a plurality of holes formed at an upper portion of the bar, the backward flow preventing bar being installed at a central portion of the heater water vessel and being connected to the subsidiary water vessel, and ii) a discharging pipe for discharging the heated water, the discharging pipe being formed at a side of the heater water vessel.

Preferably, the pressure control device has a conical shaped lower portion tapered upward and a first cylinder corresponding in size to the lower portion at an upper portion of the pressure control means. Furthermore, the pressure control device has an inlet formed between the conical shaped portion and the first cylinder, an outlet formed at an upper end of the first cylinder, and a first moving member for controlling the pressure of the heater water vessel, the first moving member being installed in the first cylinder to be moved in the upward and downward direction. In the pressure control device, the first moving member is comprised of an alloy in which tin is contained as a main component. Preferably, the alloy comprises at least one metal among copper, silver, and nickel. Also, the first moving member has a spherical shape or a piston shape.

Preferably, the main water vessel further has a pressure valve device connected to the discharging pipe so as to supply the main water vessel with the heated water from the heater water vessel at a constant pressure.

In the main water vessel, the pressure valve device further has i) a body connected to the discharging pipe, ii) a water flow portion having a discharging hole, the water flow portion being installed at a lower portion of the body, iii) a second cylinder installed on the water flow portion in the body, and iv) a second moving member installed in the second cylinder to be moved in upward and downward directions. In the pressure valve device, the second moving member has a piston shape. Furthermore, the second moving member is comprised of an alloy in which tin is contained as a main component.

Preferably, the main water vessel further has a float for detecting a water level in the main water vessel.

In the heating type ultrasonic humidifier according to the present invention, the subsidiary water vessel receives the water from the water supply vessel through the valve. The water in the subsidiary water vessel is supplied to the heater water vessel through the holes formed at the upper portion of the backward flow preventing bar, after the water has passed through the water flow pipe and the backward flow preventing bar. The water in the heater water vessel is heated by the heater, to have a predetermined temperature. Therefore, the germs existing in the water are destroyed by heating the water. When the pressure of the heater water vessel reaches the predetermined temperature, the pressure control device installed above the heater water vessel and the pressure valve device together control the pressure of the heater water vessel by the movements of the first moving member in the first cylinder and the second moving member in the second cylinder, so the heated water in the heater water vessel flows into the main water vessel through the discharging pipe. That is, when the water in the heater water vessel is not sufficiently heated, the second moving member in the second cylinder of the pressure control valve sits on a square-jawed keeper, so the water in the heater water vessel cannot flow into the main water vessel. Then, if the pressure of the heater water vessel reaches the predetermined value, the second moving member goes up and the first moving member goes down, so the heated water in the heater water vessel flows into the main water vessel.

When the water level in the main water vessel reaches the predetermined height, the float detects this and operates the ultrasonic vibrator through a control device. The ultrasonic vibrator generates water droplets or mist from the water in the main water vessel. The introduced air by the motor-blower passes through the duct, and is sprayed into room with the water droplets after the introduced air and the water droplets pass through the mist conduit pipe and the nozzle.

Therefore, in the heating type ultrasonic vibrator according to the present invention, the germs existing in the water in the heater water vessel are destroyed because the water is heated by the heater. Furthermore, the water having the temperature above the predetermined value is supplied into the main water vessel from the heater water vessel because the amount of water flowing into the main water vessel is adjusted by the pressure control device and the pressure valve device, so the efficiency of the humidifier is enhanced.

BRIEF DESCRIPTION OF THE DRAWINGS

The above objects and other advantages of the present invention will become more apparent by describing in detail the preferred embodiment of the present invention with reference to the attached drawings, in which.

DESCRIPTION OF THE PREFERRED EMBODIMENT

A description will be given below in detail to the constructions and operations of the heating type ultrasonic humidifier according to the preferred embodiment of the present invention with reference to the accompanying drawings.

Figure 1:
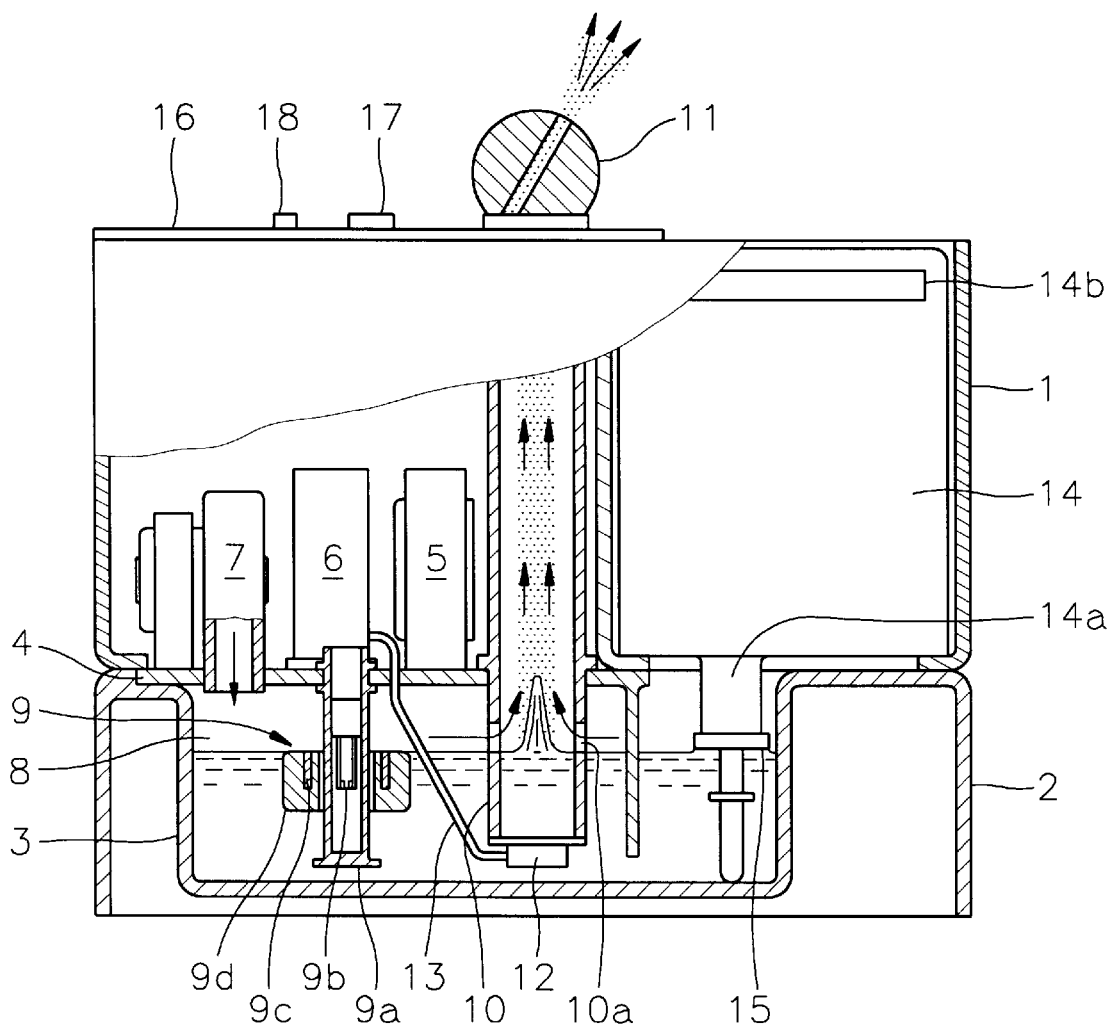
FIG. 1 is a cross-sectional view for showing a conventional ultrasonic humidifier.
Figure 2:
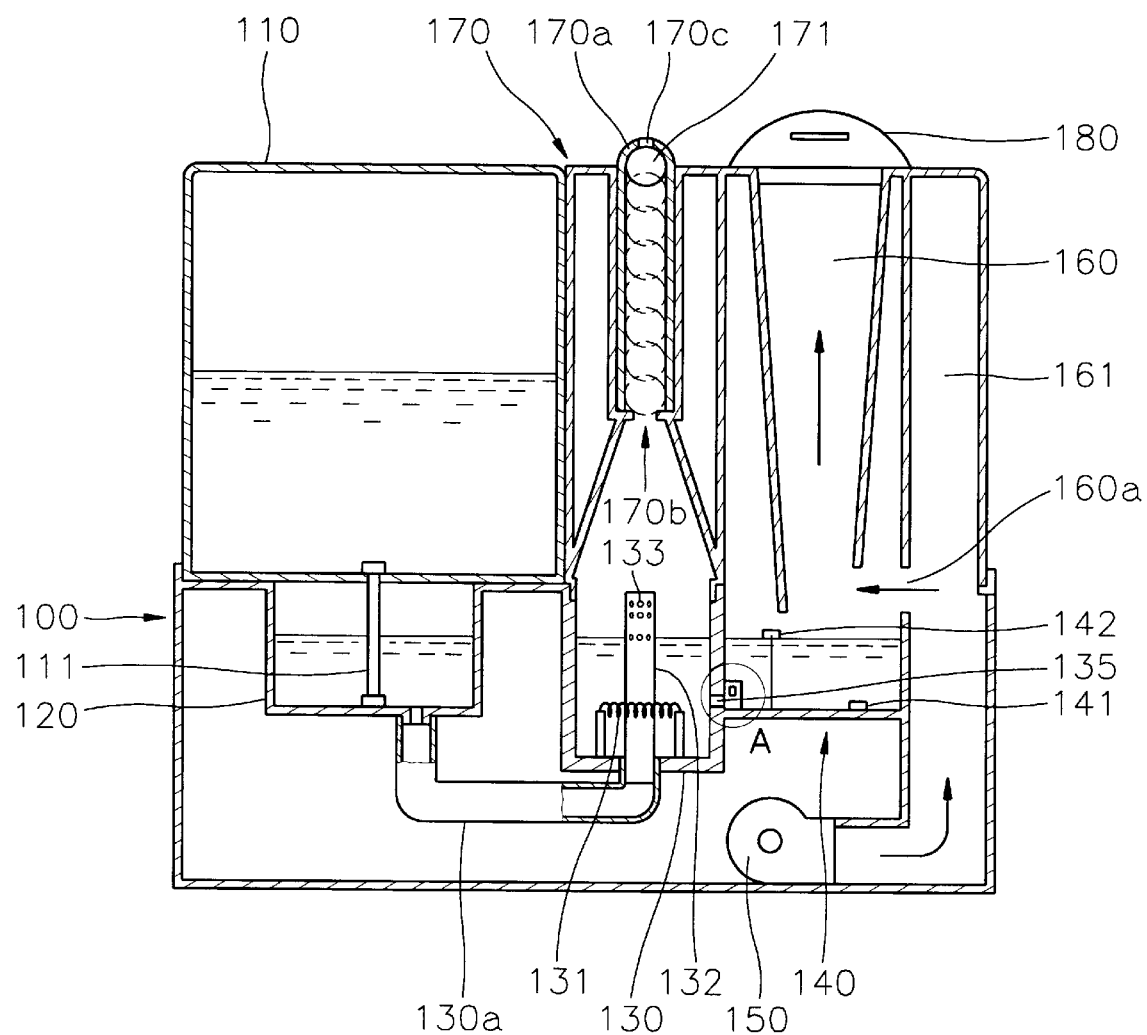
FIG. 2 is a cross-sectional view for showing a heating type ultrasonic humidifier according to one embodiment of the present invention.

FIG. 2 is a cross-sectional view for showing the heating type ultrasonic humidifier according to one embodiment of the present invention. Referring to FIG. 2, the heating type ultrasonic humidifier has a housing 100 and a water supply vessel 110 which is removably installed on a first portion of housing 100. A duct 161 is formed in a first side wall of housing 100, and a valve 111 perpendicularly installed on the lower portion of water supply vessel 110 protrudes downward to discharge a constant amount of water out of water supply vessel 110.

A subsidiary water vessel 120 for receiving the constant amount of water from water supply vessel 110 through valve 111, is installed at the first portion in housing 100 beneath water supply vessel 110. A water flow pipe 130a is formed on the lower end of subsidiary water vessel 120, so the water in subsidiary water vessel 120 is discharged through water flow pipe 130a.

A heater water vessel 130 is installed at a second portion in housing 100, and is connected to subsidiary water vessel 120 by water flow pipe 130a. A backward flow preventing bar 132 is installed at the central lower portion in heater water vessel 130 and is connected to water flow pipe 130a, to prevent the water in heater water vessel 130 from flowing backward. The lower portion of backward flow preventing bar 132 is connected to water flow pipe 130a and an upper portion of backward flow preventing bar 132 is protruded above the water level in heater water vessel 130. A plurality of holes 133 is formed at the protruded portion of backward flow preventing bar 132.

The water is supplied to heater water vessel 130 from subsidiary water vessel 120 through water flow pipe 130a and holes 133. A heater 131 is installed on a lower portion of heater water vessel 130, to heat the water in heater water vessel 130 to a predetermined temperature. Preferably, heater 131 is a top-down type heater. Also, a discharging pipe 135 is formed in a side of heater water vessel 130, to discharge the heated water by heater 131.

A pressure control device 170 for keeping the pressure of heater water vessel 130 constant by sealing heater water vessel 130, is vertically installed above the upper portion of heater water vessel 130. The lower portion of pressure control device 170 is connected to the upper portion of heater water vessel 130. Pressure control device 170 has a conical shaped lower portion which is tapered upward from the upper portion of heater water vessel 130, and a first cylinder 170a is integrally formed with the lower portion at an upper portion of pressure control device 170. An inlet 170b is formed at the lower end of first cylinder 170a, and an outlet 170c is formed at the upper end of first cylinder 170a. Also, a first moving member 171 is installed in first cylinder 170a, to control the pressure of heater water vessel 130 by moving upward and downward. First moving member 171 is comprised of an alloy which contains tin (Sn) as a main component. The alloy which contains tin has superior water resistance and is non-poisonous, and copper, silver, or nickel is added to the alloy. First moving member 171 has a spherical shape, or a piston shape, so that first moving member 171 may easily move in first cylinder 170a.

A main water vessel 140 is installed at the side of heater water vessel 130 in housing 100, and is connected to heater water vessel 130 through discharging pipe 135. A pressure valve device A is installed at the first lower corner of main water vessel 140, and is connected with discharging pipe 135. Pressure valve device A forces the heated water in heater water vessel 130 to flow into main water vessel 140 through discharging pipe 135.

Figure 3:
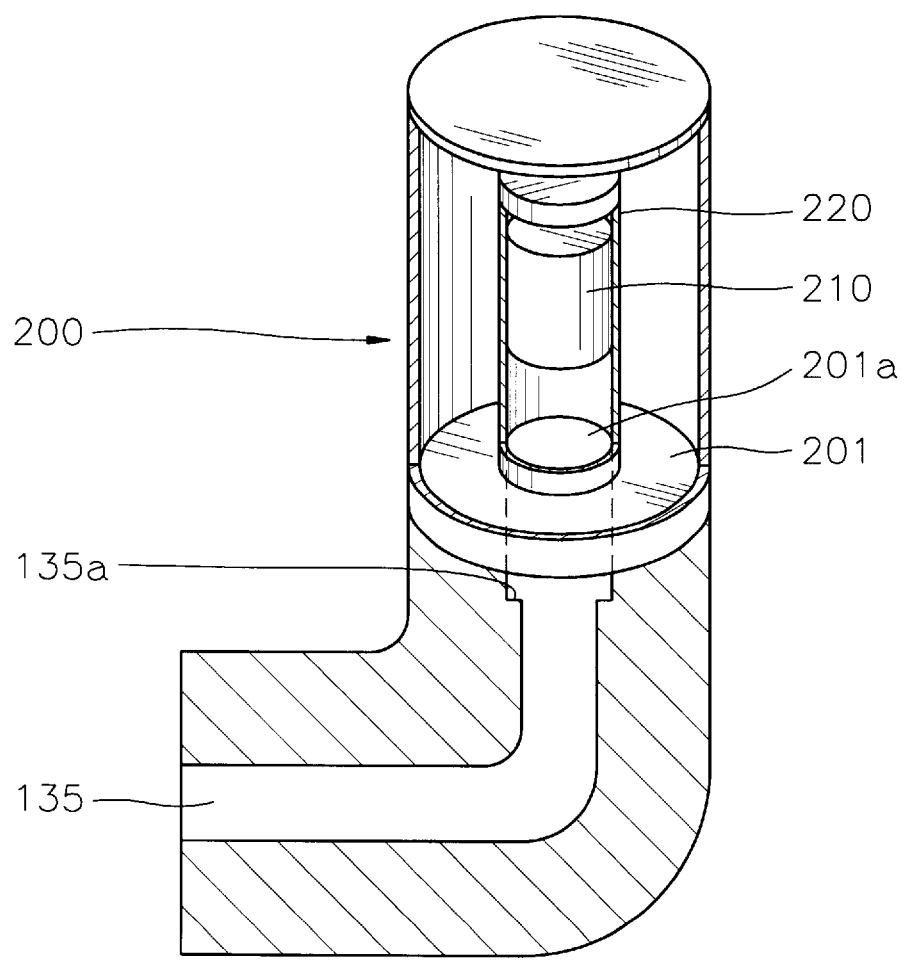
FIG. 3 is an enlarged view of a portion 'A' shown in FIG. 2.

Referring to FIG. 3, pressure valve device A has a body 200 vertically formed integrally with discharging pipe 135, a water flow portion 201 formed at the lower portion of body 200, which has a discharging hole 201a at the center thereof, a second cylinder 220 vertically installed on water flow portion 201 in body 200, and a second moving member 210 installed in second cylinder 220, which can be moved in the upward direction and in the downward direction. A square-jawed keeper 135c is formed at the portion where discharging pipe 135 is connected to body 200. Square-jawed keeper 135a supports second moving member 210, so second moving member 210 moves upward and downward in second cylinder 220 according to the pressure of water that flows into main water vessel 140 from heater water vessel 130.

Referring to FIG. 2, a float 142 for detecting the water level in main water vessel 140 is installed beside pressure valve device A in main water vessel 140, and an ultrasonic vibrator 141 is mounted on the second lower portion of main water vessel 140. Float 142 is connected to ultrasonic vibrator 141 by a control device (not shown), to operate ultrasonic vibrator 141 when the water level in main water vessel 140 reaches a predetermined value. Ultrasonic vibrator 141 supplies the water in main water vessel 140 with high frequency energy, so water droplets are generated from the surface of water in main water vessel 140.

A motor-blower 150 is installed on the lower portion of housing 100 under main water vessel 140. Motor-blower 150 supplies an air from outside to main water vessel 140 through duct 161 formed at the first side wall of housing 100. A mist conduit pipe 160 having a conical shape tapering upwards from an upper portion of main water vessel 140, is installed above the upper portion of main water vessel 140, and a nozzle 180 is installed on upper end of mist conduit pipe 160 to be rotated in all directions. Therefore, the introduced air by motor-blower 150 passes through duct 161, to be sprayed into room with the water droplets which are generated from the water in main water vessel 140 after the introduced air and the water droplets pass through mist conduit pipe 160 and nozzle 180.

It will be explained in the following that the operation of the above-described humidifier.

Subsidiary water vessel 120 receives the water from water supply vessel 110 through valve 111. The water in subsidiary water vessel 120 is supplied to heater water vessel 130 through holes 133 formed at the upper portion of backward flow preventing bar 132, after the water passes through water flow pipe 130a and backward flow preventing bar 132. The water in heater water vessel 130 is heated by heater 131, to have a predetermined temperature. Therefore, the germs existing in the water are destroyed by heating the water. When the pressure of heater water vessel 130 reaches the predetermined value, pressure control device 170 installed on heater water vessel 130 and pressure valve device A together control the pressure of heater water vessel 130 by moving first moving member 171 in first cylinder 170a and second moving member 210 in second cylinder 220, so the heated water in heater water vessel 130 flows into main water vessel 140 through discharging pipe 135. That is, when the water in heater water vessel 130 is not sufficiently heated, second moving member 210 in second cylinder 220 of pressure control valve A sits on square-jawed keeper 135, so the water in heater water vessel 130 cannot flow into main water vessel 140. But, if the pressure of heater water vessel 130 reaches the predetermined value, second moving member 210 goes up and first moving member 171 goes down, so the heated water in heater water vessel 130 flows into main water vessel 140.

When the water level in main water vessel 140 reaches the predetermined height, float 142 detects this and operates ultrasonic vibrator 141 through control device (not shown). Ultrasonic vibrator 141 generates water droplets or mist from the water in main water vessel 140. The introduced air by motor-blow 150 passes through duct 161, and is sprayed into room with the water droplets after the introduced air and the water droplets are passed through mist conduit pipe 160 and nozzle 180.

Therefore, in the heating type ultrasonic vibrator according to the present invention, the germs existing in the water in the heater water vessel are destroyed because the water is heated by the heater. Furthermore, the water having the temperature above the predetermined value is supplied into the main water vessel from the heater water vessel because the amount of water flowing into the main water vessel is adjusted by the pressure control device and the pressure valve device, so the efficiency of humidifier is enhanced.

It is understood that various other modifications will be apparent to and can be readily made by those skilled in the art without departing from the scope and spirit of this invention. Accordingly, it is not intended that the scope of the claims appended thereto be limited to the description as set forth herein, but rather that the claims be constructed as encompassing all the features of the patentable novelty that reside in the present invention, including all the features that would be treated as equivalents thereof by those skilled in the art to which this pertains.

What is claimed is:

1. A heating type ultrasonic humidifier comprising:
   a housing having a removable water supply vessel placed on a first portion in said housing, and a duct formed at a first side wall of said housing;
   a subsidiary water vessel for receiving water from the water supply vessel, said subsidiary water vessel being mounted beneath the water supply vessel at the first portion in said housing;
   a heater water vessel for receiving the water from said subsidiary water vessel, said heater water vessel being installed at a second portion in said housing and being connected to said subsidiary water vessel, said heater water vessel having a heating means for heating the supplied water, the heating means being installed on a lower portion of said heater water vessel;
   a pressure control means for sealing up said heater water vessel to keep a pressure of said heater water vessel constant, said pressure control means being installed on an upper portion of said heater water vessel;
   a main water vessel for receiving the heated water by the heating means, said main water vessel having an ultrasonic vibrator, said main water vessel being connected to said heater water vessel;
   a mist conduit pipe for discharging a mist, said mist conduit pipe being formed above said main water vessel; and
   a motor-blower for supplying said mist conduit pipe with an air through the duct, said motor-blower being mounted on a lower portion of said housing under said main water vessel.

2. The heating type humidifier as claimed in claim 1, said heater water vessel further comprising i) a backward flow preventing bar for preventing the water supplied from said subsidiary water vessel from backward flowing, the backward flow preventing bar having a plurality of holes formed at an upper portion of the bar, the backward flow preventing bar being installed at a central portion of said heater water vessel and being connected to said subsidiary water vessel, and ii) a discharging pipe for discharging the heated water, the discharging pipe being formed at a side of said heater water vessel.

3. The heating type humidifier as claimed in claim 1, wherein said pressure control means has a conical shaped lower portion tapered upward and a first cylinder corresponding in size to the lower portion at an upper portion of said pressure control means.

4. The heating type humidifier as claimed in claim 3, wherein said pressure control means has:
   an inlet formed between the conical shaped portion and the first cylinder;
   an outlet formed at an upper end of the first cylinder; and
   a first moving member for controlling the pressure of said heater water vessel, the first moving member being installed in the first cylinder to be moved in the upward direction and in the downward direction.

5. The heating type humidifier as claimed in claim 4, wherein the first moving member is comprised of an alloy in which tin is contained as a main component.

6. The heating type humidifier as claimed in claim 5, wherein the alloy comprises at least one metal selected from the group consisting of copper, silver, and nickel.

7. The heating type humidifier as claimed in claim 3, wherein the first moving member has a spherical shape or a piston shape.

8. The heating type humidifier as claimed in claim 1, said main water vessel further comprising a pressure valve means connected to the discharging pipe so as to supply said main water vessel with the heated water from said heater water vessel at a constant pressure.

9. The heating type humidifier as claimed in claim 8, the pressure valve means further comprising i) a body connected to the discharging pipe, ii) a water flow portion having a discharging hole, the water flow portion being installed at a lower portion of the body, iii) a second cylinder installed on the water flow portion in the body, and iv) a second moving member installed in the second cylinder to be moved in the upward direction and in the downward direction.

10. The heating type humidifier as claimed in claim 9, wherein the second moving member has a piston shape.

11. The heating type humidifier as claimed in claim 9, wherein the second moving member is comprised of an alloy in which tin is contained as a main component.

12. The heating type humidifier as claimed in claim 1, said main water vessel further comprising a float for detecting a water level in said main water vessel.

13. A heating type ultrasonic humidifier comprising:
a housing having a removable water supply vessel wherein a valve is mounted on a lower end of the water supply vessel placed on a first portion in said housing, and a duct formed at a first side wall of said housing;
a subsidiary water vessel for receiving water from the water supply vessel, said subsidiary water vessel being installed beneath the water supply vessel at the first portion in said housing, said subsidiary water vessel having a water flow pipe installed beneath a lower end of said subsidiary water vessel;
a heater water vessel for receiving the water from said subsidiary water vessel, said heater water vessel being installed at a second portion in said housing and being connected to said subsidiary water vessel by the water flow pipe, said heater water vessel having i) a backward flow preventing bar for preventing the water supplied from said subsidiary water vessel from backward flowing, the backward flow preventing bar having a plurality of holes formed at an upper potion of the bar, the backward flow preventing bar being installed at a central portion of said heater water vessel and being connected to the water flow pipe, ii) a heating means for heating the supplied water, the heating means being installed at a lower portion of said heater water vessel, and iii) a discharging pipe for discharging the heated water, the discharging pipe being formed at a side of said heater water vessel;
a pressure control means for sealing up said heater water vessel to keep a pressure of said heater water vessel constant, said pressure control means being installed on an upper portion of said heater water vessel, said pressure control means having a conical shaped lower portion tapered upward, a first cylinder corresponding in size to the lower portion at an upper portion of said pressure control means, an inlet formed between the conical shaped lower portion and the first cylinder, an outlet formed at an upper end of the first cylinder, and a first moving member for controlling the pressure of said heater water vessel, the first moving member being installed in the first cylinder to be moved in the upward direction and in the downward direction;
a main water vessel for receiving the heated water by the heating means, said main water vessel having a pressure valve means connected to the discharging pipe so as to supply said main water vessel with the heated water from said heater water vessel at a constant pressure, and an ultrasonic vibrator on a lower portion, said main water vessel being connected to said heater water vessel by the discharging pipe;
a mist conduit pipe for discharging a mist, said mist conduit pipe being formed above said main water vessel;
a nozzle installed on an upper end of said mist conduit pipe to be rotated in all directions; and
a motor-blower for supplying said mist conduit pipe with an air through the duct, said motor-blower being mounted on a lower portion of said housing under said main water vessel.

14. The heating type humidifier as claimed in claim 13, wherein the first moving member is comprised of an alloy which contains tin as a main component.

15. The heating type humidifier as claimed in claim 14, wherein the alloy comprises at least one metal selected from the group consisting of copper, silver, and nickel.

16. The heating type humidifier as claimed in claim 13, wherein the first moving member has a spherical shape or a piston shape.

17. The heating type humidifier as claimed in claim 13, the pressure valve means further comprising i) a body connected to the discharging pipe, ii) a water flow portion having a discharging hole, the water flow portion being formed at a lower portion of the body, iii) a second cylinder installed on the water flow portion in the body, and iv) a second moving member installed in the second cylinder to be moved in the upward direction and in the downward direction.

18. The heating type humidifier as claimed in claim 13, wherein the second moving member has a piston shape, and the second moving member is comprised of an alloy which contains tin as a main component.

19. The heating type humidifier as claimed in claim 13, said main water vessel further comprising a float for detecting a water level in said main water vessel.

20. A heating type ultrasonic humidifier comprising:
a housing having a removable water supply vessel wherein a valve is mounted on a lower end of the water supply vessel placed on a first portion in said housing, and a duct formed at a first side wall of said housing;
a subsidiary water vessel for receiving water from the water supply vessel, said subsidiary water vessel being installed beneath the water supply vessel at the first portion in said housing, said subsidiary water vessel having a water flow pipe installed beneath a lower end of said subsidiary water vessel;
a heater water vessel for receiving the water from said subsidiary water vessel, said heater water vessel being installed at a second portion in said housing and being connected to said subsidiary water vessel by the water flow pipe, said heater water vessel having i) a backward flow preventing bar for preventing the water supplied from said subsidiary water vessel from backward flowing, the backward flow preventing bar having a plurality of holes formed at an upper potion of the bar, the backward flow preventing bar being installed at a central portion of said heater water vessel and being connected to the water flow pipe, ii) a heating means for heating the supplied water, the heating means being installed at a lower portion of said heater water vessel, and iii) a discharging pipe for discharging the heated water, the discharging pipe being formed at a side of said heater water vessel;
a pressure control means for sealing up said heater water vessel to keep a pressure of said heater water vessel constant, said pressure control means being installed on an upper portion of said heater water vessel, said pressure control means having a conical shaped lower portion tapered upward, a first cylinder corresponding in size to the lower portion at an upper portion of said pressure control means, an inlet formed between the conical shaped lower portion and the first cylinder, an outlet formed at an upper end of the first cylinder, and a first moving member for controlling the pressure of said heater water vessel, the first moving member being installed in the first cylinder to be moved in the upward direction and in the downward direction;

a main water vessel for receiving the heated water by the heating means, said main water vessel having a float for detecting a water level of said main water vessel, the float being installed in said water vessel, and an ultrasonic vibrator installed on a lower portion of said main water vessel, said main water vessel being connected to said heater water vessel by the discharging pipe;

a pressure valve means having a) a body connected to the discharging pipe, b) a water flow portion having a discharging hole, the water flow portion being installed at a lower portion of the body, c) a second cylinder installed on the water flow portion in the body, and d) a second moving member installed in the second cylinder to be moved in the upward direction and in the downward direction;

a mist conduit pipe for discharging a mist, said mist conduit pipe being formed above said main water vessel;

a nozzle installed on an upper end of said mist conduit pipe to be rotated in all directions; and a motor-blower for supplying said mist conduit pipe with an air through the duct, said motor-blower being mounted on a lower portion of said housing under said main water vessel.

\* \* \* \* \*